United States Patent [19]

Horrobin

[11] Patent Number: 5,198,468

[45] Date of Patent: * Mar. 30, 1993

[54] ESSENTIAL FATTY ACID COMPOSITION

[75] Inventor: David F. Horrobin, Guildford, England

[73] Assignee: Efamol Holdings Plc, Surrey, England

[*] Notice: The portion of the term of this patent subsequent to Dec. 11, 2007 has been disclaimed.

[21] Appl. No.: 717,862

[22] Filed: Jun. 19, 1991

Related U.S. Application Data

[63] Continuation of Ser. No. 598,782, Oct. 18, 1990, abandoned, which is a continuation of Ser. No. 211,057, Jun. 24, 1988, abandoned.

[30] Foreign Application Priority Data

Jun. 24, 1987 [GB] United Kingdom ................. 8714772

[51] Int. Cl.$^5$ .............................................. A61K 31/20
[52] U.S. Cl. .................................................... 514/558
[58] Field of Search ........................................ 514/558

[56] References Cited

U.S. PATENT DOCUMENTS

| 4,355,027 | 10/1982 | Growdon et al. | 514/78 |
| 4,753,964 | 6/1988 | Horrobin | 514/558 |
| 4,810,497 | 3/1989 | Horrobin | 514/558 |
| 4,851,431 | 7/1989 | Yehuda | 514/560 |

FOREIGN PATENT DOCUMENTS

| 0115419 | 8/1984 | European Pat. Off. . |
| 0234733 | 9/1987 | European Pat. Off. . |
| 0275643 | 7/1988 | European Pat. Off. . |

OTHER PUBLICATIONS

The Merck Manual of Diagnosis and Therapy, 15th Ed. p. 1481, 1987.
Chem Abst., 106:195209n, 1987.
Chem Abst., 101:71570a, 1984.

Primary Examiner—John W. Rollins
Attorney, Agent, or Firm—Nixon & Vanderhye

[57] ABSTRACT

Treatment or prevention of memory loss with a medicament consisting of an n-6 essential fatty acid selected from GLA, DGLA, AA, adrenic acid and the 22:5 n-6 acid and an n-3 essential fatty acid selected from the 18:4 n-3 and 20:4 n-3 acids, EPA, the 22:5 n-3 acid and DHA.

2 Claims, No Drawings

ESSENTIAL FATTY ACID COMPOSITION

This is a continuation of application Ser. No. 07/598,782, filed Oct. 18, 1990, now abandoned, which is a continuation of application Ser. No. 07/211,057, filed Jun. 24, 1988, now abandoned.

The invention relates to essential fatty acid (EFA) compositions and treatments therewith.

A previous patent application (British Application No. 8601915) has dealt with the use of lithium and/or essential fatty acids (EFAs) in the treatment of dementias, including Alzheimer's disease. Memory loss can occur in the dementias, but also in many other situations such as alcoholism, chronic schizophrenia and normal ageing. We have now found that EFA supplementation as such is beneficial in memory loss.

GENERAL DISCUSSION

The bodily EFAs, falling largely into the two series known as the n-6 and n-3 EFAs of structure and relation as follows, and sharing, it is believed, common enzymes in the two pathways, are:

| n-6 | n-3 |
|---|---|
| 18:2 delta-9,12(linoleic acid) | 18:3 delta-9,12,15 (alpha-linolenic acid) |
| delta-6 desaturase ↓ | ↓ |
| 18:3 delta-6,9,12(gamma-linolenic acid) | 18:4 delta-6,9,12,15 |
| elongation ↓ | ↓ |
| 20:3 delta-8,11,14(dihomo-gamma-linolenic acid) | 20:4 delta-8,11,14,17 |
| delta-5 desaturase ↓ | ↓ |
| 20:4 delta-5,8,11,14(arachidonic acid) | 20:5 delta-5,8,11,14,17 |
| elongation ↓ | ↓ |
| 22:4 delta-7,10,13,16(adrenic acid) | 22:5 delta-7,10,13,16,19 |
| delta-4 desaturase ↓ | ↓ |
| 22:5 delta-4,7,10,13,16 | 22:6 delta-4,7,10,13,16,19 |

The acids are in the natural all-cis configuration. In the n-6 series, commonly used names for the 18:2 and 18:3 )octadeca di-enoic and tri-enoic) acids are linoleic acid and gamma-linolenic acid (GLA); for the 20:3 and 20:4 (eicosa tri-enoic and tetra-enoic) acids they are dihomo-gamma-linolenic acid (DGLA) and arachidonic acid (AA); and for the 22:4 (docosatetraenoic) acid adrenic acid. In the n-3 series only alpha-linolenic acid (ALA) (18:3) is commonly referred to by a non-systematic name but the name stearidonic acid does exist for the 18:4 n-3 acids. Initials derived from the systematic names are also used e.g. EPA for the 20:5 (eicosapentaenoic) acid but do not serve where acids of the same chain length and degree of unsaturation exist in both series e.g. the two 22:5 acids.

BACKGROUND OF THE INVENTION

The brain is particularly rich in EFAs, but the parent dietary EFAs, namely linoleic acid and alpahlinolenic acid, are present only in small amounts. These dietary EFAs must be metabolised by the enzyme delta-6-desaturase (D6D), to give (from linoleic acid) gamma-linolenic acid (GLA) and (from alpha-linolenic acid) stearidonic acid 18:4 n-3, and then to other metabolites. Because ageing, alcohol, catecholamines released during stress, and lack of certain nutritional factors have all been shown to impair D6D function, it occurred to us to see if there was a particular value for the brain in administering GLA, 18:4 n-3 and the higher acids formed from them.

EXPERIMENTAL WORK

Human studies have now been performed in two groups of patients known to suffer from memory impairment. These are alcoholics and chronic hospitalized schizophrenics. In alcoholics withdrawing from alcohol, either evening primrose oil capsules or matching placebos were administered for a period of 24 weeks. At the start and end of this period, standard Stirling memory tests were administered. Evening primrose oil was used because it is unusual among vegetable oils in containing GLA as well as linoleic acid. The patients receiving evening primrose oil improved to a greater extent than those receiving placebo.

TABLE 1

Improvements in short term and long term memory on Stirling visual memory testing in groups of matched alcoholics given either evening primrose oil or placebo for 24 weeks. Each figure shows the percentage of incorrect answers ± the standard deviation. In the change column + indicates improvement and − deterioration.

|  | GLA GROUP (n = 14) | PLACEBO GROUP (n = 14) |
|---|---|---|
| | Short Term Memory % Incorrect | |
| Start | 16.67 ± 13.20 | 14.20 ± 7.89 |
| End | 11.67 ± 11.74 | 16.82 ± 14.54 |
| Change | + 5.00 | |
| | Long Term Memory % Incorrect | |
| Start | 60.07 ± 15.37 | 55.00 ± 14.14 |
| End | 50.0 ± 21.0 | 56.82 ± 11.02 |
| Change | + 10.00 | − 1.82 |

Since linoleic acid but not GLA is present in the normal diet in substantial amounts, it is reasonable to assume that the GLA was responsible for this effect. The GLA metabolites, dihomo-gamma-linolenic acid (DGLA), arachidonic acid (AA), ardrenic acid (AdrA) and 22:5 n-6 are also present in human brain and will have similar therapeutic effects.

In a similar study in chronic hospitalized schizophrenics, GLA in the form of evening primrose oil also improved memory to a significantly greater degree than placebo, this time using the standard Weschler battery of memory tests (Table 2, 1st phase).

In the schizophrenics at the end of the first trial, a second phase trial was carried out. The purpose was to test the possible contribution of the n-3 EFAs formed from alpha-linolenic acid. Convenient sources of these include 18:4n-3 in blackcurrant seed oil and eicosapentaenoic acid (20:5n-3) and docosahexaenoic acid (22:6n-3) from fish oils. A combination of both n-6 and n-3 EFAs was given to both groups of schizophrenics, those who had been on placebo and those who had been on active treatment. The improvement in memory as assessed by the Wechsler scale was greater in the patients treated with both n-3 and n-6 EFAs than in those treated with n-6 EFAs alone (Table 2, 2nd phase).

TABLE 2

Mean changes in Wechsler Memory Quotient in groups of schizophrenics given either evening primrose oil (containing n-6 EFAs) or placebo for a period of 16 weeks (first treatment period). The figures show the change in score from baseline with a + sign indicating improvement. In a second phase of the study, both groups were given a preparation containing both n-6 and n-3 EFAs for a further 16 weeks. Further improvements were noted and again the figures show the changes from the original baseline

|  | 1st Phase | 2nd Phase |
|---|---|---|
| Placebo (n = 19) | +0.9 | +7.6 |
| Primrose oil (n = 12) | +6.1 | +9.3 |

THE INVENTION

The invention, therefore, broadly lies in:

1. A method of improving memory by the administration of one or more of each of n-6 and n-3 EFAs chosen respectively from GLA, DGLA, AA, adrenic acid and 22:5 n-6, and 18:4 n-3, 20:4 n-3, EPA, 22:5 n-3 and DHA. Doses of each fatty acid may be from 1 mg to 100 g per day, preferably in the range 10 mg to 10 g per day.

2. Preparation of medicaments for use in improving memory wherein n-6 and n-3 EFAs are associated in amounts suited to said doses.

FORMS AND SOURCES OF EFAs

When derivatives of the EFAs are used as discussed below, the amounts are calculated as the EFA.

The EFAs can be and indeed normally will be used as an assimilable, pharmacologically acceptable and physiologically equivalent derivative and reference to EFAs herein, including in the claims, is to be taken as including reference to such derivatives. Identification of useful derivatives is by their having the valuable effect in the body of the acid itself, but conversion can be shown directly by gas chromatographic analysis of concentrations in blood, body fat, or other tissue by standard techniques, for example those of Pelick et al, p. 23, "Analysis of Lipids and Lipoproteins" Ed. Perkins, American Oil Chemists Society, Champaign, Illinois, U.S.A.

Convenient derivatives of EFAs include salts, amides, esters including glyceride esters and alkyl (e.g. $C_1$ to $C_4$) esters, and phospholipids.

Thus if desired, pharmaceutical compositions may be produced for use in the invention so far as the EFA is concerned by associating the natural or synthetic acid, as such or as a derivative, with an acceptable pharmaceutical vehicle. It is, however, at present convenient to incorporate the acids into compositions in the form of available oils having a high content of the acids, hence references to "oils" herein.

Fish oils are a convenient source of n-3 EFAs, examples being fish body oils, especially of oily fish such as herring, mackerel, anchovies, pilchards, menhaden, tuna and salmon, fish gut oils, fish liver oils; oils derived from growth of certain fungi and algae; oils from animals or birds consuming fish, such as seals.

At the present time known natural oils having a high GLA acid content are few (there are no known natural sources of significant amounts of DGLA). One source of GLA currently available is the seed of Evening Primrose species such as *Oenothera biennis L.* and *Oenothera lamarckiana*, the oil extract therefrom containing GLA (about 8%) and linoleic acid (about 72%) in the form of their glycerides together with other glycerides (percentages based on total fatty acids). Other sources of GLA are Borage species such as *Borago officinalis* which, though current yield per acre is low, provide a richer source of gamma-linolenic acid than Oenothera oil. Recent studies on fungi and other micro-organisms which can be cultivated by fermentation promise a micro-organism source.

The oil is extracted from the seeds by one of the conventional methods of extraction such as cold pressure, screw pressure after partially cooking the seed or solvent extraction.

Fractionation of a typical sample of this oil in the form of methyl esters shows the relative proportions:

| Palmitate | 6.15 |
|---|---|
| Stearate | 1.6 |
| Oleate | 10.15 |
| Linoleate | 72.6 |
| Gamma-Linolenate | 8.9 |

The seed oil extracts referred to above can used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon DGLA if present.

For the n-6 series acids higher than GLA synthesis is possible though not simple, for example for DGLA. However AA and higher acids are available from slaughterhouses, for example adrenic acid from adrenal glands. Arachidonic acid is present in substantial amounts in meat.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in relation to methods of treatment and pharmaceutical compositions, but it will be understood that the EFAs, being in the nature of dietary supplements, could be incorporated in a dietary margarine or other foodstuff which when for the purposes herein is to be considered a medicament.

PHARMACEUTICAL PRESENTATION

The compositions according to the invention are conveniently in a form suitable for oral, parenteral, etc. administration in a suitable pharmaceutical vehicle, as discussed in detail for example in Williams GB-A-1,082,624 to which reference may be made, and in any case very well known generally for any particular kind of preparation. Thus, for example, tablets, capsules, ingestible liquid or powder preparations can be prepared as required. Injectable solutions of hydrolysed Oenothera oil and fish oil may be prepared using albumin to solubilise the free acid.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following are specific examples of the invention, for use in treatment or prophylaxis in man against memory loss:
1. 500 mg capsules of blackcurrant seed oil containing 90 mg GLA and 20 mg of 18:4n-3, six per day.
2. 500 mg capsules containing 300 mg ethyl-GLA and 200 mg ethyl-EPA, six per day.
3. 500 mg capsules containing 80% evening primrose oil (9% GLA and 72% linoleic acid) and 20% fish oil (18% EPA and 12% DHA), twelve per day.

I claim:
1. A method of improving memory comprising administering to a person suffering from deterioration of memory associated with schizophrenia or with physiological aging as measured by the Sterling or Weschler tests, an n-6 essential fatting acid selected from GLA, DGLA, AA, adrenic acid and the 22:5 n-6 acid and an n-3 essential fatty acid selected from the 18:4 n-3 and 20:4 n-3 acids, EPA, the 22:5 n-3 acid and DHA in an effective amount of each of the n-6 acid and the n-3 acid of 1 mg to 100 g per day.
2. A method as claimed in claim 1 in which the n-6 and n-3 acids are each administered in an effective amount of 10 mg to 10 g per day.